(12) United States Patent
Bentley et al.

(10) Patent No.: US 6,759,195 B1
(45) Date of Patent: Jul. 6, 2004

(54) METHOD OF DIFFERENTIAL DISPLAY OF PROKARYOTIC MESSENGER RNA BY RTPCR

(75) Inventors: William E. Bentley, St. Michaels, MD (US); Ryan Gill, Boston, MA (US)

(73) Assignee: University of Maryland Biotechnology Institute, Baltimore, MD (US)

(*) Notice: Subject to any disclaimer, the term of this patent is extended or adjusted under 35 U.S.C. 154(b) by 220 days.

(21) Appl. No.: 09/534,366

(22) Filed: Mar. 24, 2000

Related U.S. Application Data

(60) Provisional application No. 60/126,038, filed on Mar. 25, 1999.

(51) Int. Cl.$^7$ ............................ C12Q 1/68; C07H 21/02
(52) U.S. Cl. ............................ 435/6; 536/23.1; 536/24.3
(58) Field of Search .................... 435/6, 91.2; 536/23.1, 536/24.3, 29.31

(56) References Cited

U.S. PATENT DOCUMENTS

| | | |
|---|---|---|
| 5,021,335 A | 6/1991 | Tecott et al. |
| 5,168,038 A | 12/1992 | Tecott et al. |
| 5,262,311 A | 11/1993 | Pardee et al. |
| 5,487,985 A | 1/1996 | McClelland et al. |
| 5,580,726 A | 12/1996 | Villeponteau et al. |
| 5,599,672 A | 2/1997 | Liang et al. |
| 5,665,547 A | 9/1997 | Pardee et al. |
| 5,814,445 A | 9/1998 | Belyavsky et al. |
| 5,861,245 A | 1/1999 | McClelland et al. |
| 6,057,100 A * | 5/2000 | Heyneker ....................... 435/6 |

OTHER PUBLICATIONS

Su et al, "Optimized chemiluminescent detection of DNA amplified in the exponential phase of PCR", Biotechniques 17(4):734–736, Apr. 1994.*

Gill et al, "RTPCR differential display analysis of stress induced *E. coli* genes using a novel stress membrane", Book of Abstracts, 217 American Chemical Society National Meeting, BIOT172, Apr. 1994.*

Fislage, Dr. Rainer "Differential Display Approach to Quantitation of environmental stimuli on bacterial gene expression," *Electrophoresis* 1998, 19, 613–616.

Fislage et al., "Primer design for a prokaryotic differential display RT–PCR," *Nucleic Acids Research*, 1997, vol. 25. No. 9.

Gill et al., "Reverse Transcription–PCR Differential Display Analysis of *Escherichia coli* Global Gene Regulation in Response to Heat Shock," *Applied and Environmental Microbiology*, Dec. 1999, p. 5386–5393.

Alberts et al., "Molecular Clones," *Methods in Enzymology*, vol. 254.

Sompayrao et al., "Overcoming Limitations of the mRNA Differential Display Technique." *Nucleic Acids Research*, 1993, vol. 23, No. 22, 4738–4739.

Stacey, K.A. "*Escherichia coli*." p. 334–338.

Wan et al., "Cloning Differentially Expressed Genes by Using Differential Display and Subtractive Hybridization." *Methods in Molecular Biology*, vol. 85.

Welsh et al., "Arbitrarily Primed PCR Fingerprinting of RNA," *Nucleic Acids Research*, 1990, vol. 20. No. 19, 4965–4970.

Welsh et al., "Fingerprinting genomes using PCR with arbitrary primers." *Nucleic Acids Research,.* 1990, vol. 18. No. 24, 7213–7218.

WO 9737045 English Abstract.
WO 9849345 English Abstract.
WO 9911823 English Abstract.

Ayala et al., "New Primer Strategy Improves Precision of Differential Display." *BioTechniques*, vol. 18, No. 5 (1995).

Cash, P. "Characterization of bacterial proteomes by two–dimensional electrophoresis." *Analytica Chimica Acta*, 372: (1–2) 121–145 Oct. 19, 1998 [Abstract Only].

Chuang et al., "Characterization of Twenty–Six New Heat Shock Genes of *Escherichia coli*," *Journal of Bacteriology*, Apr. 1993, p. 5242–5252.

Chuang et al., "Global Regulation of Gene Expression in *Escherichia coli*." *Journal of Bacteriology*, Apr. 1993, p. 2026–2036.

Cox et al., "Translation of RNA to Protein." p. 914–922.

Fleming et al., "Optimization of Differential Display of Prokaryotic mRNA: Application to Pure Culture and Soil Microcosms." *Applied and Environmental Microbiology*, 1998; 64(10), 3698–3706.

Kohara et al., "The Physical Map of the Whole *E. coli* Chromosome: Application of a New Strategy for Rapid Analysis and Sorting of a Large Genomic Library," *Cell*, vol. 50, 495–508.

(List continued on next page.)

*Primary Examiner*—Jeffrey Fredman
(74) *Attorney, Agent, or Firm*—Marianne Fuierer; Yongzhi Yang; Steven J. Hultquist

(57) ABSTRACT

The present invention provides a method of differential display of prokaryotic messages RNA by RTPCR, the method comprising the steps of: adding a first primer mixture to a first nucleic acid sample including a first mixture of mRNA to form a first primer/first nucleic acid sample mixture; adding the first primer mixture to a second nucleic acid sample including a first mixture of mRNA to form a first primer/second nucleic acid sample mixture; incubating the first primer/first nucleic acid sample mixture to produce a first population of cDNA; incubating the first primer/second nucleic acid sample mixture to produce a second population of cDNA; adding a second primer to the first population of cDNA to form a second primer/first population of cDNA mixture; adding the second primer mixture to the second population of cDNA to form a second primer/second population of cDNA mixture; amplifying the second primer/first population of cDNA mixture to produce a third population of cDNA; amplifying the second primer/second population of cDNA mixture to produce a fourth population of cDNA; identifying the presence or level of mRNA in the third population of cDNA; and identifying the presence or level of mRNA in the fourth population of cDNA.

32 Claims, 6 Drawing Sheets

OTHER PUBLICATIONS

Liang et al., "Differential Display of Eukaryotic Messenger RNA by Means of the Polymerase Chain Reaction." *Science*, 1992, vol. 257, p. 967–971.

Liang et al., "Distribution and Cloning of Eukaryotic mRNAs by Means of Differential Display: Refinements and Optimization." *Nucleic Acids Research*, 1993, vol. 21, No. 14, 3269–3275.

Liang et al., "Recent Advances in Differential Display," *Immunology*, 1995, 7:274–280.

Rindi et al., "Oligo(dT)–primed synthesis of cDNA by reverse transcriptase in mycobacteria." *Biochemical and Biophysical Research Communications*. 248: (2) 216–218 Jul. 20, 1998. [Abstract Only].

Ryan T. Gill professional biography. University of Maryland Biotechnology Institute website. www.glue.umd.edu/~rtgill.

Saizieu et al., "Bacterial Transcript Imaging by Hybridization of Total RNA to Oligonucleotide Arrays." *Nature Biotechnology*, 1998; 16: 45–48.

SIGMA website advertising materials. *Sigma's New Enhanced Avian RT–PCR Kit*. www.sigma–aldrich.com/PCR.

"Solutions to Key Problems of RT–PCR." *Ambion Tech-Notes Newsletter*, vol. 6, No. 2, 6–8.

\* cited by examiner

MW_st 1 2 3 4 5 6 7 c4 c5 c6 c7 MW_st.

PCR amplified mRNA rRNA (Degraded)

c4 c5 c6 c7

Chromosomal DNA Contamination

—— Restriction Enzyme Site
▬ Heat Shock Gene Fragments
→ Heat Shock Gene Region

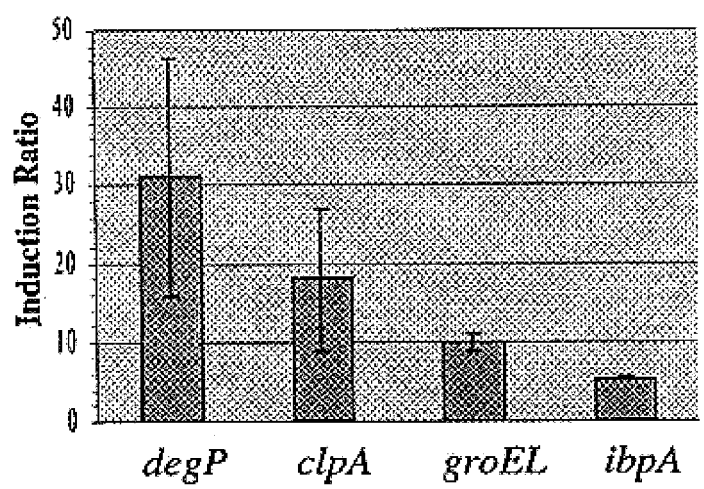
FIG. 6A
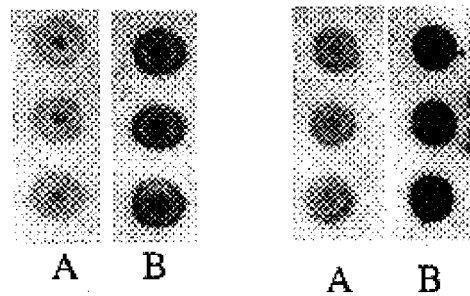
FIG. 6B     FIG. 6C
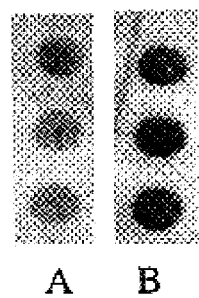 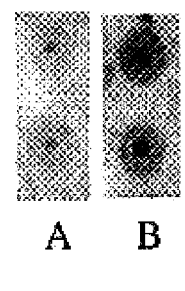
FIG. 6D     FIG. 6E

METHOD OF DIFFERENTIAL DISPLAY OF PROKARYOTIC MESSENGER RNA BY RTPCR

CROSS-REFERENCE TO RELATED APPLICATIONS

This application makes reference to the following U.S. Provisional Patent Application No. 60/126,038, entitled "Method of Differential Display of Prokaryotic Messenger RNA by RTPCR," filed Mar. 25, 1999. The entire disclosure and contents of this application are hereby incorporated by reference.

GOVERNMENT INTEREST STATMENT

This invention is made with government support under contract number DAAM01-96-0037, awarded by the United States Army. The government may have certain rights in this invention.

BACKGROUND OF THE INVENTION

1. Field of the Invention

The present invention relates to methods and materials useful for performing reverse transcription-polymerase chain reaction in prokaryotic cells.

2. Description of the Related Art

The first comprehensive studies of cellular response resulted from the development of two-dimensional gel electrophoresis and a complementary method for quantitatively measuring protein levels (O'Farell, P. H., "High Resolution Two-Dimensional Electrophoresis of Proteins", *Journal of Biological Chemistry*, 250(10):4007–21 (1975); and Pederson el al., in 1978). In parallel, Casadaban created transcriptional fusion proteins to assist in the study of gene regulation, which has been particularly useful for analyzing genes whose products are difficult to characterize (Casadaban, M. J., "Regulation of the Regulatory Gene for the Arabinose Pathway, araC", *Journal of Molecular Biology*, 104:557–66 (1976)). Both of these techniques have since been further refined (See Casadaban, M. J. et al., "Lactose Genes Fused to Exogenous Promoters in One Step Using a Mu-lac Bacteriophage: In vivo Probe for Transcriptional Control Sequences", *Proceedings of the National Academy of Sciences*, 76(9):4530–33 (1979); and see Kenyon, C. J. et al., "DNA-damaging Agents Stimulate Gene Expression at Specific Loci in *Escherichia coli*", *Proceedings of the National Academy of Sciences*, 177(5):2819–23 (1980)).

More recently, detection of transcriptional regulation has been further simplified due to such bioluminescent reporter proteins as luciferase (Rupani, S. et al, "Characterization of the Stress Response of a Bioluminescent Biological Sensor in Batch and Continuous Cultures", *Biotechnology Progress*, 12:387–92 (1996); and VanDyk, T. K. et al., "Rapid and Sensitive Pollutant Detection by Induction of Heat Shock Gene-bioluminescence Gene Fusions", *Applied Environmental Microbiology*, 60:1414–20 (1994)) and green fluorescent protein (Gill, R. T. et al., "Physiological Effects of DTT Addition to *E. coli* Including Growth Rate, Specific Oxygen Uptake, Heat Shock Protein Expression, and Specific Activity of Recombinant Protein", *Biotechnology and Bioengineering*, 59:248–59 (1998)).

In the mid-1980's, Kohara et al. developed a restriction map of 3400 λ bacteriophage clones containing segments of the *E. coli* chromosome (Kohara et al., "The Physical Map of the Whole *E. coli* Chromosome: Application of a New Strategy for Rapid Analysis and Sorting of a Large Genomic Library", *Cell*, 50:495–508 (1987)). This set was originally developed to not only map the location of *E. coli* genes but also to map and clone the gene or genes that is (are) induced in response to a certain external or internal signal(s). According to Kohara et al., their identified clones could be exploited for the isolation of any desired *E. coli* genes if their map positions were known.

Using the Kohara set of overlapping λ phage clones, Chuang el al. later demonstrated that global gene regulation in *E. coli* could be analyzed using single stranded reverse transcribed complementary DNA (hereinafter cDNA), in which radiolabeled cDNA was hybridized with the Kohara clones (Chuang, S. el al., "Global Regulation of Gene Expression in *Escherichia coli*", *Journal of Bacteriology*, 175:2026–36 (1993)). These clones, containing the entire *E. coli* genome, were used to map the location of cDNA homologs. Through follow-up Southern blotting (Southern, E. M., "Detection of Specific Sequences Among DNA Fragments Separated by Gel Electrophoresis", *Journal of Molecular Biology*, 98:503–17, (1975)), Chuang et al. identified 26 new heat shock genes for *E. coli* (Chuang, S. et al., "Global Regulation of Gene Expression in *Escherichia coli*", *Journal of Bacteriology*, 175:2026–36, (1993)). While this technique was a significant improvement over the previous methodologies of two-dimensional electrophoresis or transcriptional fusions for analyzing global genetic regulation, the messenger RNA (hereinafter mRNA) signal to total RNA noise ratio remained small.

One year later, Wong et al. applied a random arbitrary primed PCR amplification step, after reverse transcription of total RNA to detect a stress induced gene in *Salmonella typhimurium* (Wong, K. K. et al., "Stress-inducible Gene of *Salmonella typhimurium* Identified by Arbitrarily Primed PCR of RNA", *Proceedings of the National Academy of Science U.S.A.*, 91:639–43 (1994). While this technique did improve the level of mRNA signal, the signal to noise ratio did not change due to "random" amplification of RNA templates. In addition, due to the use of sequencing gels for transcript identification, this technique did not permit quantification at the genomic level.

An innovative refinement of these two methods was recently reported by de Saizieu et al., in which non-radioactively labeled total prokaryotic RNA was hybridized directly to an oligonucleotide array synthesized and bonded to a silicon chip (de Saizieu, A. et al., "Bacterial Transcript Imaging by Hybridization of Total RNA to Oligonucleotide Arrays, *Nature Biotechnology*, 16(l):45–8 (1998). This analysis, which allowed quantification for a large subset of transcribed genes, additionally required scanning confocal microscopy as RNA levels were detected as unamplified transcripts.

In the meantime, differential display techniques based on polymerase chain reaction (hereinafter PCR) amplification have advanced rapidly in eukaryotic systems due to mRNA polyadenylation that exclusively occurs in eukaryotic organisms. Reverse transcription-polymerase chain reaction (hereinafter RTPCR) (Liang, P. et al., "Differential Display of Eukaryotic Messenger RNA by Means of the Polymerase Chain Reaction", *Science*, 257:967–71 (1992)) and random arbitrary-primed polymerase chain reaction (hereinafter RAP-PCR) (Welsh, J. et al., "Arbitrarily Primed PCR Fingerprinting of RNA, *Nucleic Acids Research*", 20:4965–70 (1992)) specifically were developed in response to the problem of obtaining a small mRNA signal ratio to total RNA noise ratio. These techniques enhanced the mRNA signal to total RNA noise ratio via differential display experiments. With these techniques, the identification of differentially expressed genes among the mRNA for a pair of eukaryotes was carried out, with subsequent recovery of the cDNA and genomic clones for each eukaryote (Liang et al. 1992).

Additional developments in eukaryotic-based RTPCR/ RAP-PCR included the use of random arbitrary primers or "motif" primers, the use of sense and antisense oligonucleotide primers, usually degenerate in sequence, which were designed to amplify cDNA templates encoding proteins using particular structural motifs, and amplification products were displayed using agarose gel electrophoresis and ethidium bromide fluorescence staining (Donohue, P. et aL, *Differential Display Methods and Protocols*, Chapter 3: "Differential Display Using Random Hexamer-Primed cDNA, Motif Primers, and Agarose Gel Electrophoresis, 85: 25–35, 25–6 (Peng Liang and Arthur B. Pardee ed., 1997).

Pardee et al, U.S. Pat. No. 5,262,311, disclose a method of isolating mRNAs as cDNAs by employing a polymerase amplification method using two specific primers. This method is used in eukaryotic organisms and is known as differential display. Differential display involves amplifying partial cDNA sequences from subsets of mRNAs by reverse transcription and the polymerase reaction, then displaying these sequences on a sequencing gel.

McClelland et al., U.S. Pat. No. 5,487,985, disclose an arbitrarily primed polymerase chain reaction (hereinafter AP-PCR) for a method of generating a set of discrete DNA amplification products characteristic of a genome as a "fingerprint". This method is suitable for the identification of bacterial species, bacterial strains, mammals, and plants and utilizes a single-stranded DNA primer.

Villeponteau et al., U.S. Pat. No. 5,580,726, disclose a method and kit for enhanced differential display for eukaryotic organisms which comprises using first oligonucleotide primers for reverse transcription of mRNAs and both the first and second oligonucleotide primers for amplification of the resultant cDNAs. It is designed as a technique for screening differences in gene expression between different stages of cell development.

Liang et aL, U.S. Pat. No. 5,599,672, disclose a method of isolating mRNAs as cDNAs, by using two oligodeoxynucleotide primers of varying combinations wherein the first primer is used as a primer for reverse transcription of the mRNA and the resultant cDNA is amplified with a polymerase using both the first and second primers as a primer set.

Pardee et al, U.S. Pat. No. 5,665,547, disclose a method for comparing amounts or levels of mRNAs in eukaryotic organisms that employs a polymerase amplification method using two oligodeoxynucleotide primers of varying combinations in which the first primer is used as a primer for reverse transcription and the resultant cDNA is amplified using both the first and second primers as a primer set.

Belyavasky et al., U.S. Pat. No. 5,814,445 disclose a method of identification of differentially expressed mRNA in eukaryotic organisms by arbitrary primed RT-PCR. This consists of synthesizing, from a set of sequences of mRNA, sets of fragments of cDNA which are separated with the aid of gel electrophoresis and a detection of a marker and comparison of the separation pictures is carried out. If further detection is necessary, the separated cDNA fragments are transferred to a membrane with sequential hybridization by oligonucleotides which partially overlap the common sequence of the fragments. Additional analysis of the separation picture is available.

McClelland et al., U.S. Pat. No. 5,861,245, disclose AP-PCR as a method of generating a set of discrete DNA amplification products characteristic of a genome as a "fingerprint". This method is suitable for the identification of bacterial species, bacterial strains, mammals and plants and utilizes a single-stranded DNA primer.

SUMMARY OF THE INVENTION

It is an object of the present invention to provide a method for the rapid identification of genes with increased or decreased transcription in response to environmental stimuli.

It is another object of the present invention to provide a method that may be utilized in bioprocess fermentations as well as in basic science studies of prokaryotic global genetic regulation.

It is yet another object of the present invention to provide a kit for analysis of genetic regulation and/or the response of genes to specific stimuli.

According to a first broad aspect of the present invention, there is provided a method comprising the steps of: adding a first primer mixture comprising RT1, RT2, RT3, RT4, RT5, RT6, RT7, RT8, RT9, RT10, PCR1, PCR3 and PCR5 to a first nucleic acid sample including a first mixture of mRNA to form a first primer/first nucleic acid sample mixture; adding the first primer mixture to a second nucleic acid sample including a first mixture of mRNA to form a first primer/second nucleic acid sample mixture; incubating the first primer/first nucleic acid sample mixture to produce a first population of cDNA; incubating the first primer/second nucleic acid sample mixture to produce a second population of cDNA; adding a second primer mixture comprising RT1, RT2, RT3, RT4, RT5, RT6, RT7, RT8, RT9, RT10, PCR1, PCR2, PCR3, PCR4, PCR5, PCR6, PCR7, PCR8, PCR9, and PCR10 to the first population of cDNA to form a second primer/first population of cDNA mixture; adding the second primer mixture to the second population of cDNA to form a second primer/second population of cDNA mixture; amplifying the second primer/first population of cDNA mixture to produce a third population of cDNA; amplifying the second primer/second population of cDNA mixture to produce a fourth population of cDNA; identifying the presence or level of mRNA in the third population of cDNA; and identifying the presence or level of mRNA in the fourth population of cDNA.

According to a second broad aspect of the present invention, there is provided a composition comprising primers RT1, RT2, RT3, RT4, RT5, RT6, RT7, RT8, RT9, RT10, PCR1, PCR3, and PCR5.

According to a third broad aspect of the present invention, there is provided a composition comprising primers RT1, RT2, RT3, RT4, RT5, RT6, RT7, RT8, RT9, RT10, PCR1, PCR2, PCR3, PCR4, PCR5, PCR6, PCR7, PCR8, PCR9, and PCR10.

According to a fourth broad aspect of the present invention, there is provided a kit for enabling RTPCR of prokaryotic mRNA, comprising: a first container containing a first primer mixture comprising: RT1, RT2, RT3, RT4, RT5, RT6, RT7, RF8, RT9, RT10, PCR1, PCR3 and PCR5; and a second container containing a second primer mixture comprising: RT1, RT2, RT3, RT4, RT5, RT6, RT7, RT8, RT9, RT10, PCR1, PCR2, PCR3, PCR4, PCR5, PCR6, PCR7, PCR8, PCR9, and PCR10.

According to a fifth broad aspect of the present invention, there is provided a method comprising the steps of: adding a first primer mixture to a first nucleic acid sample including a first mixture of mRNA to form a first primer/first nucleic acid sample mixture; adding the first primer mixture to a second nucleic acid sample including a first mixture of mRNA to form a first primer/second nucleic acid sample mixture; incubating the first primer/first nucleic acid sample mixture to produce a first population of cDNA; incubating the first primer/second nucleic acid sample mixture to produce a second population of cDNA; adding a second primer mixture to the first population of cDNA to form a second primer/first population of cDNA mixture; adding the second primer mixture to the second population of cDNA to form a second primer/second population of cDNA mixture; amplifying the second primer/first population of cDNA mixture to produce a third population of cDNA; amplifying the second primer/second population of cDNA mixture to produce a fourth population of cDNA; identifying the presence or level of mRNA in the third population of cDNA using a gene plotting membrane; and identifying the presence or level of mRNA in the fourth population of cDNA using a gene plotting membrane.

Other objects and features of the present invention will be apparent from the following detailed description of the preferred embodiment.

BRIEF DESCRIPTION OF THE DRAWINGS

The invention will be described in conjunction with the accompanying drawings, in which:

FIG. 6A is a bar chart of dot blots of heat shock samples collected in triplicate under identical conditions;

FIG. 6B is a total RNA dot blot for the degP gene,

FIG. 6C is a total RNA dot blot for the clpA gene;

FIG. 6D is a total RNA dot blot for the groEL gene; and

FIG. 6E is a total RNA dot blot for the ibpA gene.

DETAILED DESCRIPTION OF THE PREFERRED EMBODIMENT

Figure 1:
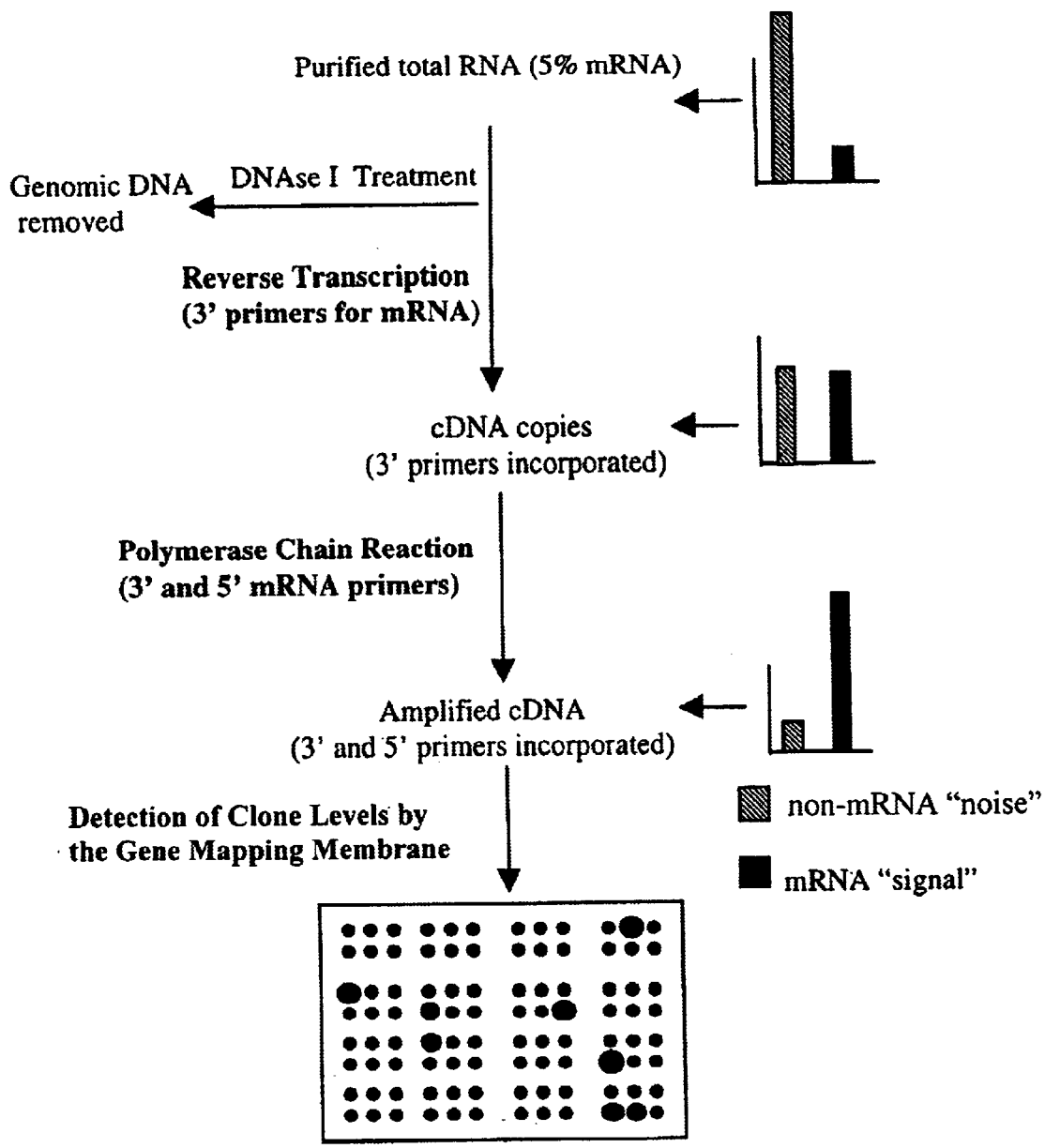
FIG. 1 is a schematic diagram of the RTPCR and gene mapping techniques of the present invention.

It is advantageous to define several terms before describing the invention. It should be appreciated that the following definitions are used throughout this application.

Definitions

Where the definition of terms departs from the commonly used meaning of the term, the definitions provided below should be utilized, unless specifically indicated.

For the purposes of the present invention, the term "hybridization" and its grammatical equivalents, when used with a maintenance time period, indicates subjecting the hybridization reaction mixture, in the context of the concentrations of reactants and accompanying reagents in the admixture, to time, temperature and pH conditions sufficient to allow the primers to anneal with the template, typically to form a nucleic acid duplex. Such time, temperature and pH conditions required to accomplish hybridization depend, as is well known in the art, on the length of the primer to be hybridized, the degree of complementarity between the primer and the template, the guanidine and cytosine content of the polynucleotide, the stringency of the hybridization desired, and the presence of salts or additional reagents in the hybridization reaction admixture as may affect the kinetics of hybridization. Methods for optimizing hybridization conditions for a given hybridization reaction admixture are well known in the art.

For the purposes of the present invention, the term "primer" as used herein refers to a polynucleotide, whether purified from a nucleic acid restriction digest or produced synthetically which is capable of acting as a point of initiation of synthesis when placed under conditions in which synthesis of a primer extension product which is complementary to a template is induced, i.e., in the presence of nucleotides and an agent for polymerization such as DNA polymerase, reverse transcriptase and the like, and at a suitable temperature and pH.

For the purposes of the present invention the term "equimolar mixture of primers" refers to a mixture of primers in which all primers are present in equal molar amounts.

Description

Since the development of RTPCR as a technique for differential display in 1992 and through further developments of the technique, differential display has not been widely utilized in prokaryotic systems due to a lack of polyadenylation at the 3' end of prokaryotic mRNA. The absence of polyadenylation prevents the initiation of cDNA by the 3'-anchored primers of the eukaryotic differential display method developed by Liang el al. However, an analogous system of differential display for prokaryotes was developed by Fislage et al. using non-anchored primers that would permit the initiation of cDNA in prokaryotes, see Fislage, R. et al., "Primer Design for a Prokaryotic Differential Display RT-PCR", *Nucleics Acids Research*, 25: (9)1830–35 (1997), the entire contents and disclosure of which is hereby incorporated by reference.

Through a detailed statistical evaluation of the coding regions extracted from bacterial genetic databases, Fislage el al. designed ten RT primers for the 3' end and ten PCR primers for the 5' end of prokaryotic mRNA. These primers have increased specificity in the 3' region and the 5' regions surrounding *E. coli* genes and decreased specificity for rRNA or other abundant small RNA species such that mRNA were preferentially transcribed. The RTPCR methodology of Fislage et al. used one RT primer in combination with a single PCR primer for an RTPCR reaction, which was subsequently repeated for each primer set so that 100 different amplifications were run for every sample. Following amplification, each sample was analyzed by gel electrophoresis, reamplification, and sequencing. Fislage el al. concluded that their primer design would be useful for differential display PCR with a genome coverage of the range 59–90% in the *Enterobacteriaeceac* group, as well as for DNA fingerprinting methods. In addition, Fislage et al. provides that especially for completely sequenced prokaryotes, transcription regulation of all genes with unknown functions may be assessed under varying environmental conditions, see also Fislage, R., "Differential Display Approach to Quantitation of Environmental Stimuli", *Electrophoresis*, 19(4):613–6 (1998), the entire contents and disclosure of which is hereby incorporated by reference.

However, the process described by Fislage et al. is a time-consuming, labor-intensive, expensive process of differential display for prokaryotes in that 100 amplifications must be carried out in order to generate the data obtained from this method. Therefore, there exists a need for a differential display for prokaryotes that could be effectively carried out in less time and that would produce as much data as was generated by Fislage et al. but with less overall expense. To that end, the present invention provides methods and materials useful for performing differential display of prokaryotic mRNA by RTPCR.

The present invention employs an RTPCR/RAP-PCR based technique that uses a novel combination of random primers specifically designed for prokaryotic mRNA to improve differential display analysis via one amplification, rather than requiring a series of amplifications until all primer combinations have been exhausted. Described below is an *E. coli* RTPCR technique that utilizes this unique combination of the primers in a degenerate fashion for mRNA-specific amplification of RNA. Accordingly, only a single amplification was required for each RNA sample and repeated amplifications of the same RNA under identical conditions were enabled for analysis of experimental error. In addition, the RTPCR method of the present invention was quantifiable by the use of a relatively inexpensive *E. coli* gene mapping membrane for global analysis of amplified RNA, rather than by agarose gel electrophoresis.

Specifically, by avoiding the use of sequencing gels, the method of the present invention avoids performing multiple amplifications of the same RNA sample. The RTPCR method of the present invention is validated, as described below, by comparison with quantified Kohara clone intensities probed with amplified RNA from heat shocked and non-heat shocked *E. coli*. Since Kohara clones contain more than one *E. coli* gene, restriction digested Kohara clones were hybridized with RTPCR products to confirm amplification of specific heat shock genes. At least 78 Kohara clones containing *E. coli* genes that are involved in stress responses and global regulation were bound to the gene mapping membrane. In addition, northern and total RNA dot blots were performed to confirm differentially displayed transcript levels.

Using the RTPCR method of the present invention for prokaryotic mRNA with the present invention's novel combination of equimolar mixtures of primers for the reactions of RTPCR, and hybridizing the DNA probes to a stress membrane for further quantification, it has been possible to realize the unexpected results of a 71% "true" hit rate for differential display experiments. This represents a significant improvement over the 50% "true" hit rate formerly established by Wan et al. (Wan, J. et al., 1997. *Differential Display Methods and Protocols*, Chapter 5: "Cloning Differentially Expressed Genes by Using Differential Display and Subtractive Hybridization", 85:45–68 (Peng Liang and Arthur B. Pardee ed., 1997). The need for identification by electrophoresis and subsequent reamplification and sequencing have been eliminated by the RTPCR methods and materials of the present invention for prokaryotic mRNA, thereby saving time, reducing labor costs, and saving significant laboratory expenses. See FIG. 1 for a schematic diagram of the RTPCR and gene mapping techniques of the present invention.

See Table 1 below for a listing of the RTPCR primers, including the SEQ ID NO for each primer, that are used in a novel combination in this invention to amplify mRNA in prokaryotic organisms. See Table 4 below for a listing of the primer sequences, including the SEQ ID NO for each of the primers, used in EXAMPLE 12.

The inducing agent may be any compound or system which will function to accomplish the synthesis of primer extension agents, including enzymes. Suitable enzymes include, for example, *E. coli*, DNA polymerase I, Klenow fragment of *E. coli* DNA polymerase I, T4 DNA polymerase, T7 DNA polymerase, recombinant modified T7 DNA polymerase described by Tabor et al., U.S. Pat. Nos. 4,942,130 and 4,946,786, other available DNA polymerases, reverse transcriptase, and other enzymes, including heat-stable enzymes, which will facilitate combination of the nucleotides in the proper manner to form the primer extension products which are complementary to each nucleic acid strand.

In a further aspect of the invention, the reagents described herein can be packaged in kit form. As used herein, the term "package" refers to a solid matrix or material customarily utilized in such a kit system in the form of at least one or more enclosure that is capable of holding within fixed limits at least one or more of the reagent components for use in a method of the present invention. Such materials include glass and plastic (e.g., polyethylene, polypropylene and polycarbonate) bottle, vials, paper, plastic and plastic-foil laminated envelopes and the like. Thus, for example, a package can be a glass vial used to contain the appropriate quantities of polynucleotide primer(s), genomic DNA, vectors, restriction enzyme(s), DNA polymerase, DNA ligase, or a combination thereof. An aliquot of each component sufficient to perform at least one complete RTPCR procedure will be provided in each container.

The primers packaged in kit form can be placed in enclosures either separately or together. When either of these occurs, the primers of the kit are present in equimolar amounts. The remaining components can be packaged in separate containers, including a dot blotted stress membrane. What will primarily dictate the packaging of the primers in kit form will be the number of steps anticipated at the time of the RTPCR reaction, and the number of tubes expected that the entire reaction will require before completion of the reaction.

More concisely, two-step, two-tube RTPCR techniques are particularly useful when amplifying multiple targets from a single cDNA synthesis reaction. In a two-step technique, the cDNA synthesis is performed by the RT under optimal conditions, followed by PCR amplification with an appropriate thermostable DNA polymerase. The reaction tube must be opened after cDNA synthesis to add the PCR reagents or the synthesized cDNA is transferred to a second tube for the PCR portion of the procedure. If the former occurs, the RTPCR reaction is known as a two-step, one-tube procedure. The latter is known as a two-step, two-tube RTPCR.

One-step, one-tube format RTPCR includes all reagents necessary to carry out cDNA synthesis and high-fidelity PCR amplification in a convenient one-tube format. In this format, both reactions take place successively during an uninterrupted thermal-cycling program. This format is highly desirable because of the convenience, ease of performing the reaction with only one step in one tube, greater speed of the reaction and reduced risk of contamination. Usually a buffer that is common to both RT and PCR reactions is included with this format of RTPCR.

Kits useful for producing a primer extension product for amplification of a specific nucleic acid sequence using a primer extension reaction methodology also typically include, in separate containers within the kit, dNTPs where N is adenine, thymine, guanine and cytosine, and other like agents for performing primer extension reactions.

The reagent species of any system described herein can be provided in solution, as a liquid dispersion or as a substantively dry powder, e.g., the primers may be provided in lyophilized form.

In order that the invention as described herein may be more fully understood, the following examples are set forth. It should be understood that the following examples are for illustrative purposes only and are not to be construed as limiting the invention.

EXAMPLE 1

E. coli Fermentation and Media Preparation

E. coli W3110 [pIL2] (F−, λ−, in(rrnD-rrnE)) was obtained from Dr. Yuji Kohara. W3110 previously had been utilized by Kohara el al in the creation of the Kohara miniset. The growth of E. coli was performed in LB media (Rodriguez and Tait, 1983) supplemented with 0.1 mg/ml ampicillin. The optimum growth temperature was 37° C. Experiments were performed in 250 ml shake flasks. Shake flask experiments were run in either an air shaker (New Brunswick Scientific, Edison, N.J.) at 250 rpm or a reciprocating water bath shaker (New Brunswick Scientific) at 100 rpm.

EXAMPLE 2

Induction of Stress Response and Sample Preparation

Induction of heat shock was performed in mid-exponential phase growth. Control samples of 25 ml were taken from the shake flask immediately prior to heat shock application. Heat shock was initiated by transferring shake flask cultures grown at 37° C. to a 42° C. water bath. Post-heat shock samples of 25 ml were taken 15 minutes after stress induction from the shake flask. The control and heat shock samples were immediately mixed with an equal volume of crushed ice in 50 ml centrifuge tubes. The samples were centrifuged at 5000×g for 15 minutes at 4° C., washed once in ice cold 50 mM Tris Buffer (pH=7.5), and re-pelleted under the same conditions prior to isolation of total RNA.

EXAMPLE 3

RNA Isolation and Purification

RNA isolation and purification was performed using the RNAqueous total RNA isolation kit (Ambion Inc., Austin, Tex.). This kit typically purifies 10 □g of total RNA for every ml of E. coli culture at an Optical Density (hereinafter OD) of 1.0. The purified RNA was incubated with 50 U/ml DNAse I (Boehringer Mannheim, Indianapolis, Ind.) at 37° C. for 30 minutes to remove chromosomal DNA. The purified RNA was then re-purified using the RNAqueous kit. This has been shown to produce RNA at a purity level sufficient for subsequent RTPCR (Smith, 1997).

EXAMPLE 4

Reverse Transcription Reaction

A listing of the RT primers utilized for the RT reaction is indicated in Table 1, below.

For the reverse transcription reaction, a mixture containing equimolar quantities of each RT primer was utilized. PCR primers 1, 3, and 5 were also added to this mixture at an equimolar level. The total number of primers for this reaction was 13 primers.

The reverse transcriptase reaction mixture included:

Avian myeoblastosis virus reverse transcriptase (hereinafter AMVRT) reaction buffer (50 mM Tris HCl, pH=8.3, 30 mM KCl, 8 mM $MgCl_2$)(Boehringer Mannheim);

0.5 mM deoxynucleotide mixture (Boehringer Mannheim);

0.8 U/µl RNAse inhibitor (Boehringer Mannheim);

0.5 U/µl AMVRT (Boehringer Mannheim);

0.5 µM each RT primers 1–10 and PCR primers 1, 3, and 5 (Life Technologies, Gaithersburg, Md.);

15 ug RNA sample; and autoclaved deionized water to a total volume of 60 µl.

The reverse transcription reaction was performed in a Peltier Thermal Cycler (MJ Research, Watertown, Mass.). The RNA was denatured at 70° C. for 10 minutes prior to mixing with the reaction solution. The RNA templates were allowed to anneal to the added primers for 10 minutes at 25° C. prior to beginning elongation. The elongation reaction lasted for 3 hours at 42° C. Final denaturation was carried out at 95° C. for 10 minutes and cDNA was stored at −20° C.

TABLE 1

RTPCR Primers

| RT Primer | Sequence 5'-3' | PCR Primer | 5'-3' |
|---|---|---|---|
| RT1 (SEQ ID NO:1) | TTTTATCCAGC | PCR1 (SEQ ID NO:11) | GCTGGAAAAA |
| RT2 (SEQ ID NO:2) | ACTTTACGCAG | PCR2 (SEQ ID NO:12) | GCTGCTGGCG |
| RT3 (SEQ ID NO:3) | TTTATCCAGCG | PCR3 (SEQ ID NO:13) | GAAGTGCTGG |
| RT4 (SEQ ID NO:4) | TCAGCGTTTA | PCR4 (SEQ ID NO:14) | TGGCGGCGGC |
| RT5 (SEQ ID NO:5) | TTTCAGCGCCT | PCR5 (SEQ ID NO:15) | AACTGGCGAA |
| RT6 (SEQ ID NO:6) | TTTTTTCAGCA | PCR6 (SEQ ID NO:16) | ATGCGCTGGC |
| RT7 (SEQ ID NO:7) | TCTTTTTTACC | PCR7 (SEQ ID NO:17) | TGCCGATGAA |
| RT8 (SEQ ID NO:8) | ATCATCCAGCA | PCR8 (SEQ ID NO:18) | CTGGAAGAAG |
| RT9 (SEQ ID NO:9) | TTTTACCCAGC | PCR9 (SEQ ID NO:19) | ATGGCGCTGG |
| RT10 (SEQ ID NO:10) | TTCAGCCAGCG | PCR 10 (SEQ ID NO:20) | ATGGCGATGA |

EXAMPLE 5

Polymerase Chain Reaction

A listing of the PCR primers utilized for the PCR reaction is indicated in Table 1 above.

For the polymerase chain reaction, a mixture containing equimolar quantities of each PCR primer was utilized. In addition, each of the RT primers was also added to this mixture at an equimolar level. The total number of primers for this reaction was 20 primers.

The polymerase chain reaction mixture included: Taq DNA Polymerase reaction buffer (10 mM Tris HCl, pH=8.3, 50 mM KCl, 1.5 mM $MgCl_2$)(Boehringer Mannheim); 0.5 mM dATP, dCTP, dTTP, and dGTP (Boehringer Mannheim); 0.5 $\mu$M of each RT primer (Life Technologies); 0.5 $\mu$M of each PCR primer (Life Technologies); 0.05 U/$\mu$l Taq DNA Polymerase (Boehringer Mannheim); 5 $\mu$l cDNA; and autoclaved deionized water to a total volume of 60 $\mu$l.

The polymerase chain reaction was performed in an Peltier Thermal Cycler (MJ Research). The PCR cycle consisted of an initial denaturation at 94° C. for 4 minutes, followed by 40 cycles of denaturation at 94° C. for 1 minute, annealing at 40 ° C. for 1 minute, and extension at 72° C. for 1.5 minutes. A final extension at 72° C. for 5 minutes was performed.

Purification of the *E. coli* and RTPCR probe DNA was performed by ethanol/sodium acetate precipitation (following the protocol of Boehringer Mannheim). Quantification of PCR products was performed by absorbance at 260 nm.

EXAMPLE 6

2% Agarose Gel Electrophoresis of RTPCR Probe DNA

The ability of the RTPCR primers of Fislage et al. to hybridize in a degenerate fashion was compared to the use of random hexamers for differential display analysis. For these experiments, the reverse transcription reactions were incubated 2 or 4 hours, followed by 10 or 30 PCR cycles. The best results, which yielded the greatest number of bands on agarose gels, were obtained when random hexamers were used for the RT reaction and an equimolar mixture of the 10 PCR primers of Fislage et al. were used for the PCR. These primers, however, did not preferentially amplify mRNA so that an abundance of rRNA was amplified which confounded later analysis. When the primers of Fislage et al. were used as described by Fislage et al., mRNA was preferentially targeted but in the experiments described below, the lowest number of bands was observed.

After a systematic analysis of several primer combinations and incorporation of several new primers, one combination appeared most effective for amplifying mRNA to a significant level. When PCR1, PCR3 and PCR5 primers were combined with RT1, RT2, RT3, RT4, RT5, RT6, RT7, RT8, RT9, and RT10 primers for the RT reaction (13 total primers) and the RT1, RT2, RT3, RT4, RT5, RT6, RT7, RT8, RT9, and RT10 primers were combined with PCR1, PCR2, PCR3, PCR4, PCR5, PCR6, PCR7, PCR8, PCR9, and PCR10 primers for the PCR reaction, multiple bands at high concentration were noted when analyzed by 2% agarose gel electrophoresis and ethidium bromide fluorescence staining. See FIG. 2A for the results of 2% agarose gel of RTPCR samples from heat shocked and control cells. Table 2 below summarizes the procedure and the data generated when 2% agarose gel electrophoresis and ethidium bromide fluorescence staining were done.

TABLE 2

Summary of 2% Agarose Gel Electrophoresis

| Lane No. | Sample Type | Observation |
|---|---|---|
| 1 | Control (non-heat shocked) RNA | |
| 2 | Heat shocked RNA | |
| 3 | RT product of Control of Lane 1 | |
| 4 | RT product of heat shocked RNA of Lane 2 | |
| 5 | RTPCR product of Control of Lane 3 | Broad ethidium bromide bands correspond to RTPCR amplified cDNA |
| 6 | RTPCR product of heat shocked Lane 4 | Broad ethidium bromide bands correspond to RTPCR amplified cDNA |
| 7 | RTPCR product of heat shocked Lane 4 | Broad ethidium bromide bands correspond to RTPCR amplified cDNA |
| c4 | PCR product from Lanes 1 and 2 without RT (Control) (tRNA) | No distinct contamination bands for chromosomal DNA |
| c5 | RTPCR product without initial template RNA (Control) | |
| c6 | RTPCR product (tRNA) without AMVRT (Control) | No distinct contamination bands for chromosomal DNA |
| c7 | PCR without DNA Taq Polymerase (Control) | |

Further explanation of the control lanes c4 to c 7 as indicated in Table 2 is as follow: lane c4 contains PCR amplified total RNA without the RT reaction (to determine if there was DNA contamination of the purified RNA); c5 contains RTPCR product in the absence of any RNA template (to determine contamination in RT and PCR solutions); c6 contains RTPCR amplified total RNA performed without AMVRT (to ensure total RNA degradation during RTPCR which otherwise might appear on the gel); and c7 contains PCR product of total RNA without any Taq polymerase (to assess total RNA degradation during PCR).

Figure 2A:
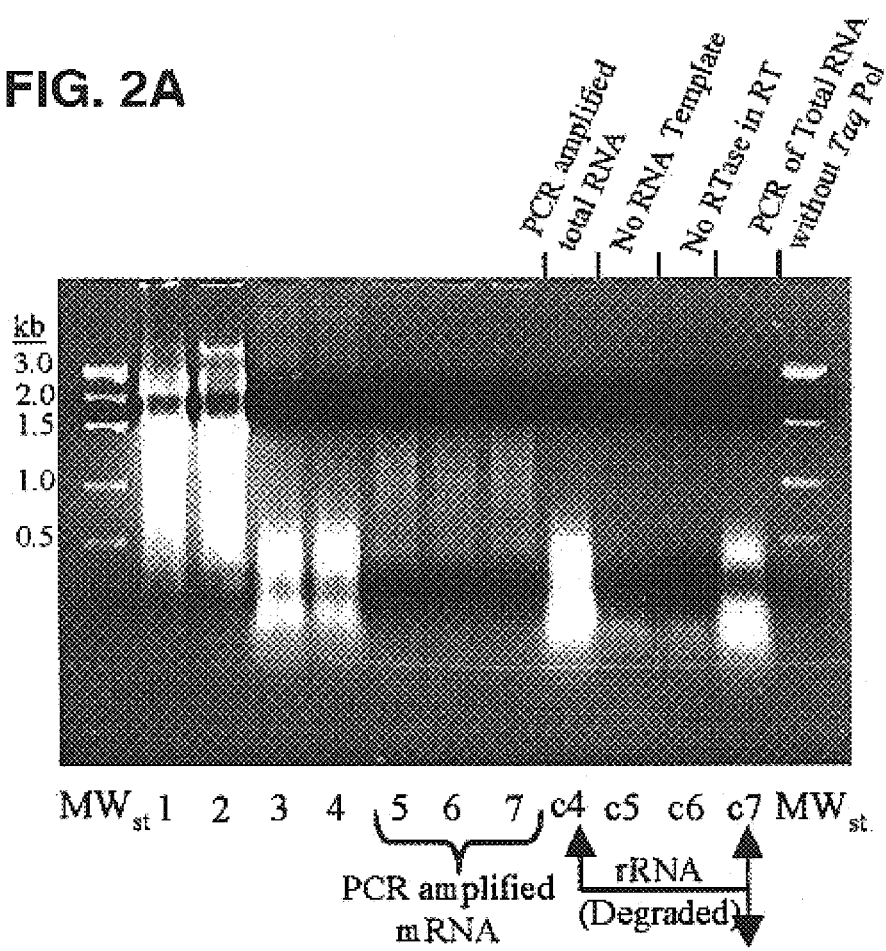
FIG. 2A illustrates the results of a first 2% agarose gel electrophoresis performed on RTPCR samples from heat shocked and control cells.

Comparison of control lanes c4, c6, and c7 of FIG. 2A allowed for the determination of whether the amplified RTPCR product was from purified RNA or contaminating DNA. Since lane c4 matched lane c7, RTPCR amplification of RNA had occurred, but because lane c4 did not match lane c6, there was no contamination of purified RNA with DNA. Lanes c4 and c6 have no distinct contamination bands in this region, therefore, there was no contaminating chromosomal DNA. The RNA-only control of lane c4 closely resembled the result when RNA was added to the PCR in the absence Taq DNA polymerase of lane 7. In this case, visualized bands corresponded to RNA fragments degraded during the PCR. Therefore, the higher molecular weight bands in lanes 5, 6, and 7 correspond to RTPCR amplified RNA, not degraded RNA or amplified chromosomal DNA.

Figure 2B:
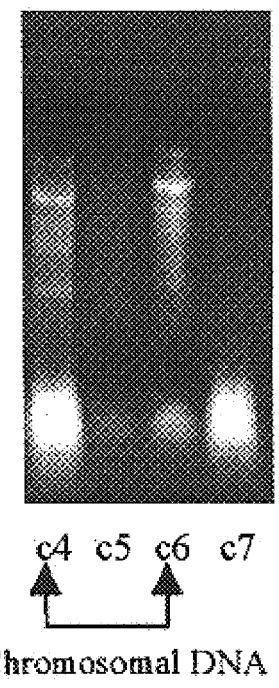
FIG. 2B illustrates the results of a second 2% agarose gel electrophoresis performed on RTPCR samples from heat shocked and control cells.

A repeat trial of the 2% agarose gel electrophoresis was performed with new RNA samples that were loaded in the same manner as in FIG. 2A. See FIG. 2B for the results of the identical control lanes c4–c7 from this agarose gel. When RNA was added to the PCR without RT, amplification produced multiple bands of product cDNA between 0.2-1 Kbp in control lanes c4 and c6. The multiple bands in these lanes were evidence of the presence of DNA contamination in the newly purified RNA samples.

The RTPCR procedure was utilized to amplify mRNA out of total RNA from both heat shocked and control cells. Specifically, the total RNA, cDNA, and RTPCR products are shown in lanes 1–7. Distinct bands were observed in the RTPCR product lanes as well as the appearance of differential levels of similar size bands between the RTPCR products from control and heat shocked cells. While significant information was obtained from the gel electrophoresis studies discussed above, the results do not indicate if the amplification that occurred is indicative of the relative abundance of mRNA transcripts. To determine this, RTPCR products were evaluated for a well-characterized stress response, the heat shock response, using a gene mapping membrane.

EXAMPLE 7

3' End-Labeling of RTPCR Probe DNA with DIG-dUTP

The 3' end labeling reaction mixture consisted of the following components: 25 $\mu$g RTPCR probe DNA; 50 U Terminal Transferase (Boehringer Mannheim); Terminal Transferase Reaction (Boehringer Mannheim); 20 $\mu$M dATP (Boehringer Mannheim); 3 $\mu$M DIG-dUTP (Boehringer Mannheim); and $CoCl_2$ (Boehringer Mannheim).

The reaction mixture was placed in a 37° C. water bath and incubated for 45 minutes. The digoxigenin (hereinafter DIG) labeled probe was purified by ethanol/sodium acetate precipitation (following the protocol of Boehringer Mannheim) and quantified by absorbance at 260 nm.

The signal strength resulting from end-labeling was evaluated and was found to be a sufficient signal for chemi-luminescent detection using the gene mapping membrane, thereby avoiding radioisotopes. Two factors investigated to make this determination were the ability of terminal transferase to 3' end-label DNA of the size expected of RTPCR products at 200–800 basepairs and the ability of DIG end-labeled probes to allow visualization of the Kohara clones on the gene mapping membrane. The efficiency of end-labeling on the RTPCR products was evaluated by dot blotting which clearly revealed a strong signal from end-labeled RTPCR products. To determine the stringency required for detection of clones on the gene mapping membrane, hybridization of 3' DIG end-labeled λ DNA that had been restriction digested to sizes similar to RTPCR products, was performed. Each Kohara clone was visible on the gene mapping membrane, thereby validating the detection method.

EXAMPLE 8

Gene Mapping Membrane Construction

The *E. coli* gene mapping membrane consists of the Kohara set of clones bound to a nylon membrane in an ordered matrix (Panvera Inc., Milwaukee, Wis.). This membrane was prepared by dot blotting the Kohara clones in an ordered fashion to a nylon membrane (Boehringer Mannheim, Indianapolis, Ind.). The gene mapping membranes underwent UV irradiation cross-linking and were allowed to air dry. The air-dried membranes were then ready for hybridization and development.

EXAMPLE 9

Hybridization and Detection of Amplified mRNA

The *E. coli* gene mapping membranes were prehybridized for 3 hours in 15 ml of prehybridization/hybridization solution (Boehringer Mannheim). The prehybridization solution was decanted and 5 ml of fresh prehybridization/hybridization solution was added.

DNA was added to the hybridization mixture at concentrations between 200–1500 ng/ml. Hybridization occurred overnight at 40–65° C. and the membranes were developed according to DIG development protocols (as recommended by Boehringer Mannheim) utilizing anti-DIG Alkaline Phosphatase (Boehringer Mannheim) and CSPD chemiluminescent substrate (Boehringer Mannheim). The developed membranes were incubated at 37° C. for 30 minutes and then exposed to X-ray film for 2 hours.

Figure 3A:
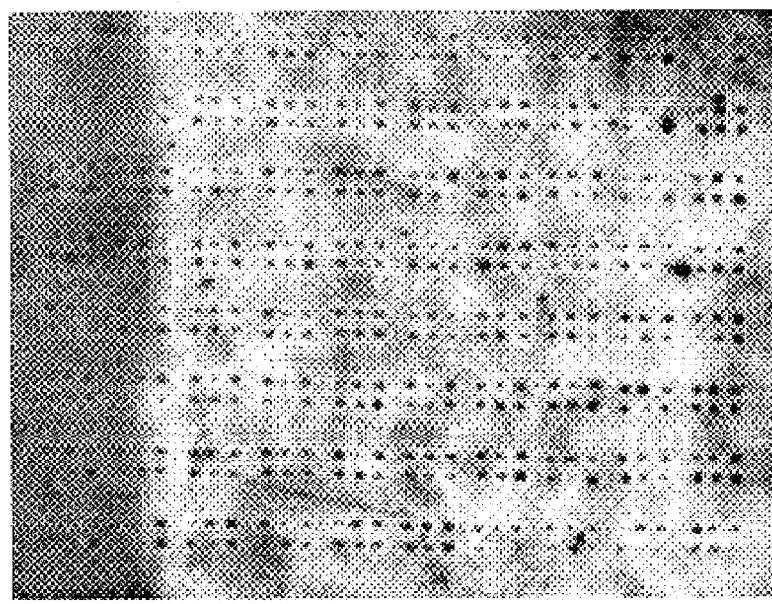
FIG. 3A illustrates the hybridization of RTPCR product from heat shocked cells into an *E. coli* gene mapping membrane.

In order to quantify and map RTPCR product levels, hybridization of the end labeled RTPCR products to the gene mapping membrane was performed. See FIG. 3A for the hybridization of RTPCR product from heat shocked cells into the *E. coli* gene mapping membrane. As all of the Kohara clones were clearly visible on all of the analyzed films, this indicated that amplified mRNA fragments representing the entire *E. coli* genome were hybridized and detected on the membrane.

The signal to noise ratio for the mRNA was high enough to provide quantification of signal at each clone location. Interestingly enough, the signal for the mRNA for all 630 clones evaluated was constant to within 1%. In addition, the signals from the clones containing rRNA genes were not the maxima of all of the clones analyzed, thereby reaffirming the ability of the RTPCR primers to preferentially amplify non-rRNA.

EXAMPLE 10

Quantification of RTPCR Product Signal

Signal quantification was performed using Scion Image Analysis Software (Frederick, Md.). X-ray films were analyzed by determining the signal strength for each Kohara clone that contained a known heat shock gene and two adjacent Kohara clones. For example, clones 101, 201, and 301 were evaluated due to the presence of the dnaKJ gene on clone 101 (clones 201 and 301, which are non-heat shock containing clones, were directly adjacent). These three Kohara clones were scanned simultaneously to minimize quantification error. To obtain an "induction ratio" the following set of calculations was performed.

First, the quantified signal intensity for each clone was divided by the average signal for all evaluated clones on the same film. This accounted for film-to-film variation in intensity and served as an internal control. Second, the signal intensity of a clone derived from heat shocked cells was divided by that of the non-heat shocked control. Third, to account for RTPCR amplification error, the induction ratios from parallel experiments were averaged for each clone. In each case, a minimum of three parallel experiments was included. Finally, for convenience, the data was normalized to an average induction ratio of 1 by dividing each clone value by the average induction ratio of all clones.

As a result, any systematic error in RT, PCR, or hybridization that would occur between experiments or membranes was eliminated. Error analysis was performed to determine the level of significance. Specifically, the normalized intensity for each clone was averaged for repeated experiments and the standard error was calculated as the standard deviation of the mean divided by the clone's average intensity. To be considered "significantly induced", a clone must have had an induction ratio greater than 1+the standard deviation of the error for that clone. To be considered "significantly repressed", a clone must have a value less than 1−the standard deviation of the error for that clone. An induction ratio of precisely 1 indicates that the clone signal did not change after heat shock. Those clones with an induction ratio of 1 were classified as "stable". Table 3 below contains the results of quantification of RTPCR product signal.

Figure 3B:
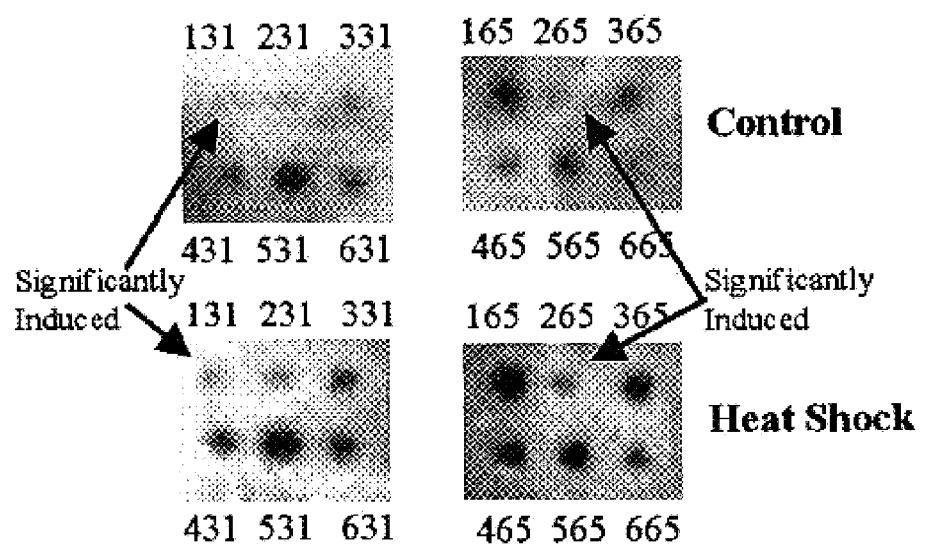
FIG. 3B illustrates the gene mapping results for control and heat shocked films for the regions containing various clones.

See FIG. 3B for the gene mapping results for control and heat shocked films for the regions containing clones 131 and 265. The significantly induced clones 131 and 265 are visible in the heat shock films but are not visible in the control films. In addition, as seen below in Table 3, after quantification and analysis of repeated measurements, the induction ratios for these two clones were greater than 1.

TABLE 3

Significantly Induced or Repressed Clones and their Induction Ratios

| Induced Clone | Induction Ratio | Repressed Clone | Induction Ratio |
|---|---|---|---|
| 131 | 4.8 +/− 0.6 | 258 (pspA) | 0.23 +/− 0.1 |
| 566 (ibpAB) | 4.6 +/− 2.5 | 675 | 0.40 +/− 0.1 |
| 117 (degP) | 3.9 +/− 1.3 | 232 (hslD) | 0.40 +/− 0.2 |
| 212 (clpA) | 3.3 +/− 0.2 | 639 | 0.45 +/− 0.2 |
| 152 (htpG) | 2.1 +/− 0.2 | 449 | 0.46 +/− 0.2 |
| 265 (hslIJ) | 1.8 +/− 0.2 | 549 | 0.48 +/− 0.3 |
| 248 | 1.8 +/− 0.6 | 547 | 0.49 +/− 0.4 |
| 537 | 1.7 +/− 0.3 | 160 | 0.49 +/− 0.1 |
| 334 (hslK) | 1.7 +/− 0.6 | 410 | 0.50 +/− 0.1 |
| 648 (groESL, hslW) | 1.6 +/− 0.1 | 638 | 0.51 +/− 0.3 |
| 448 | 1.5 +/− 0.3 | 575 | 0.51 +/− 0.2 |
| 234 | 1.3 +/− 0.2 | 509 (rpoD) | 0.52 +/− 0.2 |
| 652 (hslXYZ) | 1.2 +/− 0.1 | 302 | 0.52 +/− 0.4 |
| 233 (hslD) | 1.2 +/− 0.1 | 132 | 0.56 +/− 0.3 |

The results of quantification of RTPCR product signal indicated that nine of the fourteen significantly induced clones contained known heat shock genes and several contained multiple heat shock genes. For example, clone 566 contains the ibpA and ibpB genes and clone 648 contains the groES, groEL, and hslW genes. Of particular interest was the histogram analysis that revealed that 71% of the significantly induced clones contained heat shock genes. This was in contrast to the significantly repressed clones, of which only 28% contained known heat shock genes. Importantly, 87% of the clones evaluated had either stable or significantly repressed induction ratios. This would be expected during the heat shock response due to RNA polymerase sequestering by the heat shock sigma factor $\sigma_{32}$ (Gross, C. A., "Function and Regulation of the Heat Shock Proteins", 1382–99, in *Escherichia coli* and Salmonella: Cellular and Molecular Biology, $2^{nd}$ ed., American Society for Microbiology, Washington, D.C., (F. C. Neidhardt ed., 1996).

The benefit of using clone specific error analysis was realized when evaluating the results of induction ratios. For example, Kohara clone 233 had an induction ratio of only 1.2, however, its error was relatively small, thereby allowing its classification as significantly induced.

Figure 4A:
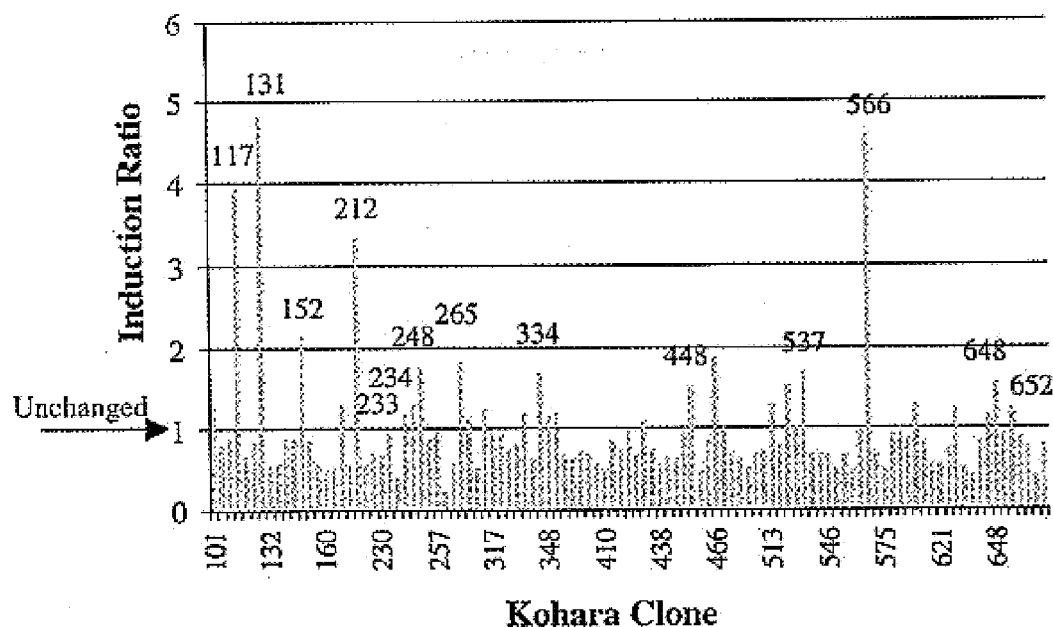
FIG. 4A is a graphical representation of the induction ratios for analyzed Kohara clones.
Figure 4B:
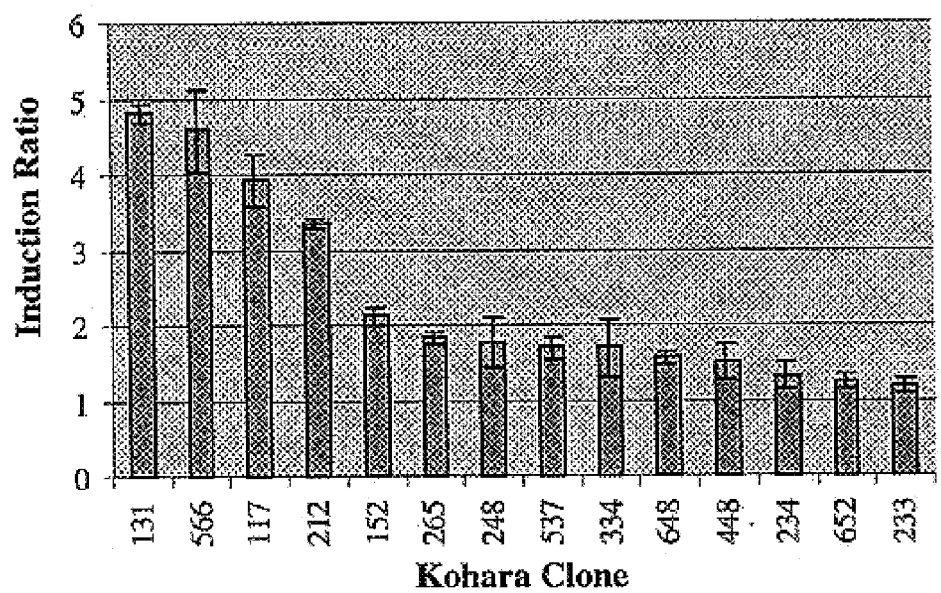
FIG. 4B is bar chart of the induction ratio and percentage error for each of the significantly induced clones identified in FIG. 4A.

See FIG. 4A for graphical representation of the induction ratios for all of the Kohara clones analyzed. The clones that are identified on the graph by number at the point where their final induction ratios are noted are considered significantly induced. The area designated as unchanged on the graph represents those clones whose induction ratio is 1. See FIG. 4B for the bar chart of the induction ratio and percentage error for each of the significantly induced clones identified in FIG. 4A. It was noted that the error bars of significantly induced clones did not cross the induction ratio of 1. As can be seen in FIG. 4B, each significantly induced clone had an induction ratio minus its standard error that was greater than one.

EXAMPLE 11

Southern Blot Analysis

The Kohara clones were amplified using the RTPCR method as noted in EXAMPLE 4 and 5. λ DNA was purified using a λ DNA purification kit (Promega Inc., Madison, Wis.). A subset of the significantly induced Kohara clones derived in EXAMPLE 10 were restriction digested to either isolate previously identified heat shock genes and/or to provide DNA fragments less than 3 Kbp. These clones were restriction digested to sizes similar to RTPCR products prior to loading into agarose gel. Each clone was run twice in adajacent lanes of the same gel.

DNA, separated by agarose gel electrophoresis, was denatured by submersion in denaturation solution (0.5 M NaOH, 1.5 M NaCl) for 30 minutes. The gel was neutralized in neutralization solution (0.5 M Tris-HCl, pH=7.5, 3 M NaCl) for 30 minutes prior to blotting. Blotting occurred overnight on a Nylon membrane (Boehringer Mannheim) in 20×SSC (3 M NaCl, 300 mM Sodium Citrate, pH=7) buffer. The DNA was fixed to the membrane using UV irradiation induced cross-linking and the membrane was stored at −20° C.

DIG end-labeling development procedures of EXAMPLE 7 and hybridization of this membrane with RTPCR products of EXAMPLE 9 were identical to those used for the gene mapping membrane constructed in EXAMPLE 8.

Southern blots against restriction digested Kohara clones were done to ensure that amplified Kohara clone signals were the result of heat shock genes, as opposed to other genes contained within the each clone. See FIGS. 5A and 5B for the results of Southern blot using restriction digested Kohara clones 117 and 212 and probing with RTPCR amplified RNA from heat shocked *E. coli*. The adjacent lanes run for each clone can be distinguished. Restriction maps for each clone are shown next to the Southern blot. Restriction sites are noted by thin horizontal lines along the restriction map. Restriction enzymes are noted below the clone number. Genes and their location on each clone's restriction fragments are as indicated on FIGS. 5A and 5B. The dark vertical bars on each restriction map indicate the fragment(s) detected by the Southern blot.

Figure 5A:
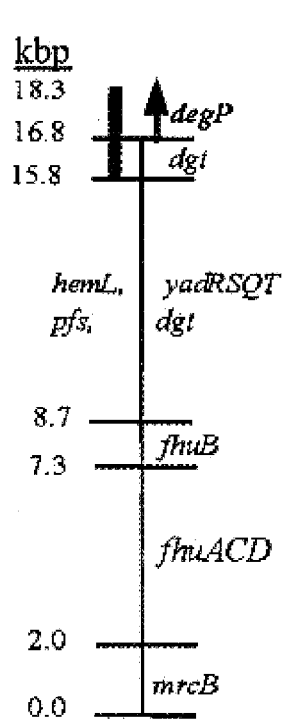
FIG. 5A illustrates the results of Southern blot using restriction digested Kohara clone 117 and probing with RTPCR amplified RNA from heat shocked *E. coli;*
Figure 5A:
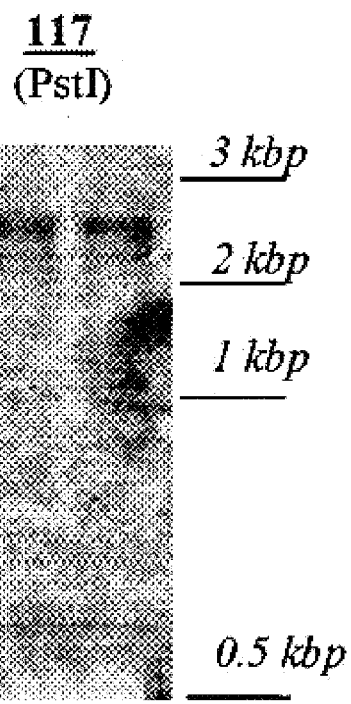
Figure 5B:
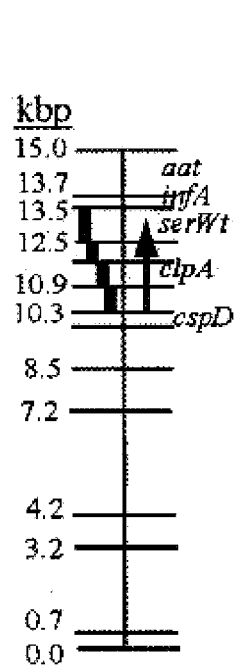
FIG. 5B illustrates the results of Southern blot using restriction digested Kohara clone 212 and probing with RTPCR amplified RNA from heat shocked *E. coli;*
Figure 5B:
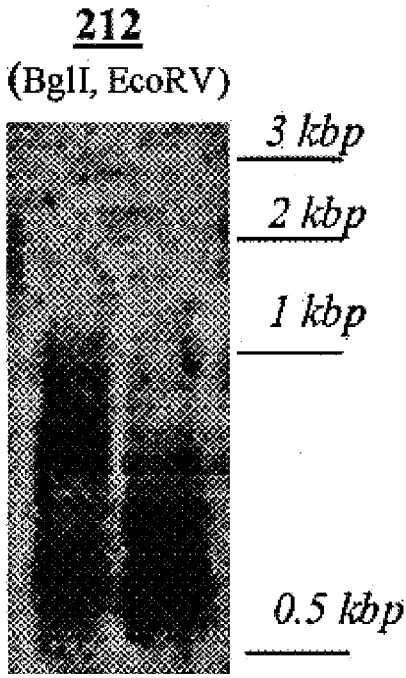

From FIG. 5A, a single 2.5 Kbp fragment was detected for clone 117. Kohara clone 117 has been reported to contain the heat shock degP gene (Berlyn, M. K. B. et al., "Linkage Map of *Escherichia coli* K-12", Edition 9, 1715–1902, in *Escherichia coli* and Salmonella: Cellular and Molecular Biology, $2^{nd}$ ed., American Society for Microbiology, Washington, D.C. (F. C. Neidhardt ed., 1996), however, the *E. coli* linkage map indicates that degP is located on clones 118 and 119. Therefore, the DNA band located at 2.5 Kbp which was found on the highly induced clone 117, could be either degP or a DNA fragment containing a potentially new heat shock gene.

In addition, a smear of fragments corresponding to 2×0.6 Kbp and 2×1.0 Kbp fragments was visible for clone 212. Kohara clone 212 contains the heat shock clpA gene which was located on two 0.6 Kbp and two 1.0 Kbp fragments after restriction digestion. Therefore, the signal detected was a broad smear with two distinct band ends between 0.6 to 1.0 Kbp corresponding to hybridization of the RTPCR heat shock product and the clpA gene of *E. coli*.

Southern blots were also performed against clones 152 and 265 and the identified fragments mapped correctly to heat shock gene regions previously identified by Chuang and Blattner. On the other hand, clone 131 contains the argF gene and multiple putative genes of unknown function as determined from a database search of Entrez available at <http://www.ncbi.nlm.nih.gov>. Southern blotting mapped the RTPCR product to yagP, however, Northern blotting did not confirm differential display. This was an example of a false positive.

EXAMPLE 12

Northern Blotting

Total RNA samples (10 µg/well) were separated using a 1% agarose denaturing gel (17% formaldehyde) at 75V for approximately 2 hours. The gel was cut to remove unused regions and blotting to a nylon membrane (Boehringer Mannheim) was performed at 4° C. overnight in 20X SSC. Total RNA dot blots were prepared by pipetting 1–5 ug of total RNA samples (in 50% formamide, 6.5% formaldehyde, 1×SSC) directly onto nylon membranes using a microsample filtration manifold (Schleicher and Schuell, Keene, N. H). All nylon membranes were fixed by UV irradiation induced cross-linking. Hybridization with DIG end-labeled Northern probes and DIG-development procedures of EXAMPLE 7 were identical to those used for the gene mapping membrane of EXAMPLE 8.

The Northern probes were prepared using the PCR DIG Probe Synthesis Kit (Boehringger Mannheim) and were approximately 400 bp in length. For quantification of Northern or total RNA dot blots, a detailed standard curve of serially diluted DIG-labeled λ DNA was utilized. The dilution spanned a 50-fold difference in mass of DNA per dot and the resulting standard curve had an $r^2=0.9$. The Northern blots were performed against ibpA and groEL genes to correlate with dot blot data and to check for probe sensitivity.

The primer sequences used to prepare each probe were as found below in Table 4.

TABLE 4

Primer Sequences for Northern Blot

| N. Blot Primer | Sequence 5'-3' |
| --- | --- |
| clpA (SEQ ID NO:21) | ATGCTCAATCAAGAACT |
| clpA (SEQ ID NO:22) | AAAGTTCACCACATCGA |
| ibpA (SEQ ID NO:23) | ATGCGTAACTTTGATTT |
| ibpA (SEQ ID NO:24) | TTAGTTGATTTCGATAC |
| groEL (SEQ ID NO:25) | ATGGCAGCTAAAGACGT |
| groEL (SEQ ID NO:26) | CTTTGTCCATCGCTTCA |
| degP (SEQ ID NO:27) | TTTAATGACCGTCGCGT |
| degP (SEQ ID NO:28) | CCACATTAGCACTGAGT |

Northern dot blots were performed against clpA, degP, ibpA and groEL genes to confirm differential transcript levels between the heat shocked and control samples. In each case the level of transcript increased significantly after heat shock. The level of degP increased 31-fold, clpA increased 18-fold, groEL increased 10-fold, and ibpA increased 5-fold. The clones that contained these genes, 117 (degP), 212 (clpA), 648 (groEL), and 566 (ibpA) were also all significantly induced. It was noted that the induction ratios calculated via dot blot were not the same as those calculated via RTPCR mapping, although this should not be expected as the RTPCR mapping technique is not gene specific. Interestingly, however, that the relative degree of induction was similar between the two analytical approaches.

See FIGS. 6B, 6C, 6D and 6E for total RNA dot blots for degP, clpA, ibpA, and groEL genes. The data in the bar chart shown in 6A are from dot blots of heat shock samples collected in triplicate under identical conditions. Signal levels for each dot were quantified and averaged for each sample. The induction ratios were then calculated as the average signal for each heat shock sample divided by the corresponding average control signal. For each dot blot, "A" is the control and "B" is from the heat shocked cells. It was noted that the dark dot within each of the dot blots is the result of the particular apparatus used in these experiments.

In summary, the combination of the Southern, Northern, and total RNA dot blot data confirmed that RTPCR amplification and the Kohara clone based analysis performed here was indicative of the relative abundance of mRNA in the original total RNA sample. Other conclusions can be drawn, such as PCR amplifies signal to noise ratio, random primers allow for global analysis and gene mapping membranes are used for rapid identification of genes.

The methods and materials disclosed and claimed herein can be made and executed without undue experimentation in light of the present disclosure. While the methods and materials of this invention has been described in terms of preferred embodiments, it will be apparent to those of skill in the art that variations may be applied to the method and in the steps or in the sequence of steps of the method and materials described herein without departing from the concept, spirit and scope of the invention. More specifically, it will be apparent that certain agents that are both physiologically and chemically related might be substituted for the agents described herein while the same or similar results would be achieved. All such similar substitutes and modifications apparent to those skilled in the art are deemed to be within the spirit, scope and concept of the invention as defined by the appended claims.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for differential display analysis of mRNA via a single amplification, the method comprising the steps of:

adding a reverse transcription reaction first primer mixture comprising 13 random 10 and 11mer primers in equal molar amounts selected from the group consisting of RT1, RT2, RT3, RT4, RT5, RT6, RT7, RT8, RT9, RT10, PCR1, PCR3 and PCR5 to a first nucleic acid sample including a first mixture of mRNA to form a first primer/first nucleic acid sample mixture;

adding said first primer mixture to a second nucleic acid sample including a first mixture of mRNA to form a first primer/second nucleic acid sample mixture;

incubating said first primer/first nucleic acid sample mixture to produce a first population of cDNA;

incubating said first primer/second nucleic acid sample mixture to produce a second population of cDNA;

adding a PCR amplification reaction second primer mixture comprising 20 random 10 and 11mer primers in equal molar amounts selected from the group consisting of RT1, RT2, RT3, RT4, RT5, RT6, RT7, RT8, RT9, RT10, PCR1, PCR2, PCR3, PCR4, PCR5, PCR6, PCR7, PCR8, PCR9, and PCR10 to said first population of cDNA to form a second primer/first population of cDNA mixture;

adding said second primer mixture to said second population of cDNA to form a second primer/second population of cDNA mixture;

amplifying said second primer/first population of cDNA mixture to produce a third population of cDNA;

amplifying said second primer/second population of cDNA mixture to produce a fourth population of cDNA;

identifying the presence or level of mRNA in said third population of cDNA, wherein the first mixture of mRNA was amplified in a single amplification; and identifying the presence or level of mRNA in said fourth population of cDNA, wherein the second mixture of mRNA was amplified in a single amplification.

2. The method recited in claim 1, wherein said first primer/first nucleic acid sample mixture is incubated at 42° C. for 3 hours to produce said first population of cDNA and said first primer/second nucleic acid sample mixture is incubated at 42° C. for 3 hours to produce said second population of cDNA.

3. The method recited in claim 1, wherein said first primer mixture comprises an equimolar mixture of primers.

4. The method recited in claim 1, wherein said first primer mixture comprises a GC content of about 48%.

5. The method recited in claim 1, wherein said second primer mixture comprises an equimolar mixture of said primers.

6. The method recited in claim 1, wherein said second primer mixture comprises a GC content of about 54%.

7. The method recited in claim 1, wherein said third population of cDNA and said fourth population of cDNA are purified with an ethanol/sodium acetate precipitation.

8. The method recited in claim 1, wherein said third population of cDNA and said fourth population of cDNA are end-labeled at the 3' end with DIG-duTP.

9. The method recited in claim 1, wherein said third population of cDNA and said fourth population of cDNA are each purified using ethanol/sodium acetate precipitation.

10. The method recited in claim 1, further comprising a step of detecting a difference in the presence or level of an individual cDNA in said third population of cDNA as compared to the presence or level of said individual cDNA in said fourth population of cDNA.

11. The method recited in claim 1, wherein a nucleotide sequence of at least one primer in said first primer mixture includes a sequence substantially complementary to a sequence found in a mRNA of known sequence.

12. The method recited in claim 1, wherein at least one cDNA in said third and fourth populations of cDNA has a size in the range of 200–800 basepairs.

13. The method recited in claim 1, further comprising a step of isolating an individual cDNA whose presence or level differs in said third and said fourth populations of cDNA.

14. The method of claim 1, wherein the presence or level of mRNA in said third population of cDNA is identified using a gene mapping membrane and the presence or level of mRNA in said fourth population of cDNA is identified using a gene mapping membrane.

15. A reverse transcription reaction composition for use in a single amplification mRNA analysis comprising 13 non-anchoring random 10 and 11mer primers selected from the group consisting of primers RT1, RT2, RT3, RT4, RT5, RT6, RT7, RT8, RT9, RT10, PCR1, PCR3, and PCR5.

16. The composition recited in claim 15, wherein said composition consists essentially of primers RT1, RT2, RT3, RT4, RT5, RT6, RT7, RT8, RT9, RT10, PCR1, PCR3, and PCR5.

17. The composition recited in claim 15, wherein said primers are directed to a reverse transcription reaction.

18. The composition recited in claim 15 wherein said composition comprises an equimolar mixture of said primers.

19. A PCR amplification reaction composition for use in a single amplification mRNA analysis comprising 20 non-anchoring random 10 and 11mer primers selected from the group consisting of RT1, RT2, RT3, RT4, RT5, RT6, RT7, RT8, RT9, RT10, PCR1, PCR2, PCR3, PCR4, PCR5, PCR6, PCR7, PCR8, PCR9, and PCR10.

20. The composition of claim 19, wherein said composition consists essentially of primers RT1, RT2, RT3, RT4, RT5, RT6, RT7, RT8, RT9, RT10, PCR1, PCR2, PCR3, PCR4, PCR5, PCR6, PCR7, PCR8, PCR9, and PCR10.

21. The composition recited in claim 19, wherein said primers are directed to a polymerase chain reaction.

22. The composition mixture recited in claim 19, wherein said composition comprises an equimolar mixture of said primers.

23. A kit for a single amplification process enabling RTPCR of prokaryotic mRNA, comprising:

a first container containing a reverse transcription reaction first primer mixture comprising 13 non-anchoring random 10 and 11mer primers selected from the group consisting of RT1, RT2, RT3, RT4, RT5, RT6, RT7, RT8, RT9, RT10, PCR1, PCR3, and PCR5; and a second container containing a PCR amplification reaction second primer mixture comprising 20 non-anchoring random 10 and 11mer primers selected from the group consisting of RT1, RT2, RT3, RT4, RT5, RT6, RT7, RT8, RT9, RT10, PCR1, PCR2, PCR3, PCR4, PCR5, PCR6, PCR7, PCR8, PCR9, and PCR10.

24. The kit recited in claim 23, wherein said first primer mixture comprises an equimolar mixture and said second primer mixture comprises an equimolar mixture.

25. The kit recited in claim 23, further comprising, in separate containers: reverse transcriptase; reverse transcriptase buffer; DNA polymerase; DNA polymerase buffer; control RNA; and dot blotted gene mapping membrane.

26. The kit recited in claim 23, wherein said RTPCR is two-step, two-tube.

27. The kit recited in claim 23, wherein said first container and said second container are enclosed in a single enclosure.

28. The kit recited in claim 24, further comprising:

a third container containing a reverse transcription reaction third primer mixture comprising 13 non-anchoring random 10 and 11mer primers selected from the group consisting of RT1, RT2, RT3, RT4, RT5, RT6, RT7, RT8, RT9, RT10, PCR1, PCR3, and PCR5; and a fourth container containing a PCR amplification reaction fourth mixture of primers comprising 20 non-anchoring random 10 and 11mer primers selected from the group consisting of RT1, RT2, RT3, RT4, RT5, RT6, RT7, RT8, RT9, RT10, PCR1, PCR2, PCR3, PCR4, PCR5, PCR6, PCR7, PCR8, PCR9, and PCR10.

29. The kit recited in claim 28, wherein said first container and said second container are enclosed in a first enclosure and said third container and said fourth container are enclosed in a second enclosure.

30. A method for analysis of mRNA via a single amplification, the method comprising the steps of:

adding a reverse transcription reaction first primer mixture comprising 13 non-anchoring random 10 and 11mer primers selected from the group consisting of RT1, RT2, RT3, RT4, RT5, RT6, RT7, RT8, RT9, RT10, PCR1, PCR3, and PCR5 to a first nucleic acid sample including a first mixture of mRNA to form a first primer/first nucleic acid sample mixture;

adding said first primer mixture to a second nucleic acid sample including a first mixture of mRNA to form a first primer/second nucleic acid sample mixture;

incubating said first primer/first nucleic acid sample mixture to produce a first population of cDNA;

incubating said first primer/second nucleic acid sample mixture to produce a second population of cDNA;

adding a PCR amplification reaction second primer mixture comprising 20 non-anchoring random 10 and 11mer primers selected from the group consisting of RT1, RT2, RT3, RT4, RT5, RT6, RT7, RT8, RT9, RT10, PCR1, PCR2, PCR3, PCR4, PCR5, PCR6, PCR7, PCR8, PCR9, and PCR10 to said first population of cDNA to form a second primer/first population of cDNA mixture;

adding said second primer mixture to said second population of cDNA to form a second primer/second population of cDNA mixture;

amplifying said second primer/first population of cDNA mixture to produce a third population of cDNA;

amplifying said second primer/second population of cDNA mixture to produce a fourth population of cDNA;

identifying the presence or level of mRNA in said third population of cDNA using a gene plotting membrane, wherein the first mixture of mRNA was amplified in a single amplification; and identifying the presence or level of mRNA in said fourth population of cDNA using a gene plotting membrane, wherein the second mixture of mRNA was amplified in a single amplification.

31. A method of differential display of prokaryotic messenger RNA by reverse transcriptase polymerase chain reaction for an RNA sample, comprising the steps of reverse transcription reaction with 3' primers for mRNA to yield corresponding cDNA, conducting polymerase chain reaction with 3' and 5' mRNA primers, to yield amplified cDNA, and hybridization of the amplified cDNA with a gene mapping membrane, for quantification of resulting RT-PCR product, wherein said method includes only a single amplification of the RNA sample wherein equimolar quantities of reverse transcription and polymerase chain reaction primers are utilized for reverse transcription and PCR, respectively, wherein the reverse transciption primers comprise RT primers of SEQ ID NO:1-SEQ ID NO:10 with PCR primers SEQ ID NO:11, SEQ ID NO:13 and SEQ ID NO:15 being present in the reverse transcription reaction in equimolar concentrations, and wherein the PCR primers include PCR primers of SEQ ID NO:11-SEQ ID NO:20, said method being devoid of electrophoretic gel processing.

32. The method according to claim 1, wherein the 10 and 11mer primers are non-anchoring.

* * * * *

UNITED STATES PATENT AND TRADEMARK OFFICE
CERTIFICATE OF CORRECTION

PATENT NO.     : 6,759,195 B1
DATED          : July 6, 2004
INVENTOR(S)    : Bently et al.

It is certified that error appears in the above-identified patent and that said Letters Patent is hereby corrected as shown below:

Column 1,
Line 34, "el" should be -- et --

Column 2,
Lines 10 and 15, "el" should be -- et --

Column 6,
Lines 46 and 56, "el" should be -- et --

Column 7,
Line 1, "el" should be -- et --

Column 9,
Line 30, "el" should be -- et --

Signed and Sealed this

Seventeenth Day of August, 2004

JON W. DUDAS
*Acting Director of the United States Patent and Trademark Office*

SEQUENCE LISTING

<160> NUMBER OF SEQ ID NOS: 28

<210> SEQ ID NO 1
<211> LENGTH: 11
<212> TYPE: DNA
<213> ORGANISM: Artificial Sequence
<220> FEATURE:
<223> OTHER INFORMATION: Description of Artificial Sequence: synthesized

<400> SEQUENCE: 1
ttttatccag c                                                          11

<210> SEQ ID NO 2

-continued

```
<211> LENGTH: 11
<212> TYPE: DNA
<213> ORGANISM: Artificial Sequence
<220> FEATURE:
<223> OTHER INFORMATION: Description of Artificial Sequence: synthesized

<400> SEQUENCE: 2
actttacgca g                                                          11

<210> SEQ ID NO 3
<211> LENGTH: 11
<212> TYPE: DNA
<213> ORGANISM: Artificial Sequence
<220> FEATURE:
<223> OTHER INFORMATION: Description of Artificial Sequence: synthesized

<400> SEQUENCE: 3
tttatccagc g                                                          11

<210> SEQ ID NO 4
<211> LENGTH: 11
<212> TYPE: DNA
<213> ORGANISM: Artificial Sequence
<220> FEATURE:
<223> OTHER INFORMATION: Description of Artificial Sequence: synthesized

<400> SEQUENCE: 4
tcagcgtttt a                                                          11

<210> SEQ ID NO 5
<211> LENGTH: 11
<212> TYPE: DNA
<213> ORGANISM: Artificial Sequence
<220> FEATURE:
<223> OTHER INFORMATION: Description of Artificial Sequence: synthesized

<400> SEQUENCE: 5
tttcagcgcc t                                                          11

<210> SEQ ID NO 6
<211> LENGTH: 11
<212> TYPE: DNA
<213> ORGANISM: Artificial Sequence
<220> FEATURE:
<223> OTHER INFORMATION: Description of Artificial Sequence: synthesized

<400> SEQUENCE: 6 tttttcagc a                                                           11

<210> SEQ ID NO 7
<211> LENGTH: 11
<212> TYPE: DNA
<213> ORGANISM: Artificial Sequence
<220> FEATURE:
<223> OTHER INFORMATION: Description of Artificial Sequence: synthesized

<400> SEQUENCE: 7
tcttttttac c                                                          11

<210> SEQ ID NO 8
<211> LENGTH: 11
<212> TYPE: DNA
<213> ORGANISM: Artificial Sequence
<220> FEATURE:
<223> OTHER INFORMATION: Description of Artificial Sequence: synthesized

<400> SEQUENCE: 8
```
atcatccagc a                                                    11

<210> SEQ ID NO 9
<211> LENGTH: 11
<212> TYPE: DNA
<213> ORGANISM: Artificial Sequence
<220> FEATURE:
<223> OTHER INFORMATION: Description of Artificial Sequence: synthesized

<400> SEQUENCE: 9
ttttacccag c                                                    11

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: synthesized

<400> SEQUENCE: 10
ttcagccagc g                                                    11

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: synthesized

<400> SEQUENCE: 11
gctggaaaaa                                                      10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: synthesized

<400> SEQUENCE: 12
gctgctggcg                                                      10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: synthesized

<400> SEQUENCE: 13
gaagtgctgg                                                      10

<210> SEQ ID NO 14
<211> LENGTH: 10
<212> TYPE: DNA
<213> ORGANISM: Artificial Sequence
<220> FEATURE:
<223> OTHER INFORMATION: Description of Artificial Sequence: synthesized

<400> SEQUENCE: 14
tggcggcggc                                                      10

<210> SEQ ID NO 15
<211> LENGTH: 10
<212> TYPE: DNA

```
<213> ORGANISM: Artificial Sequence
<220> FEATURE:
<223> OTHER INFORMATION: Description of Artificial Sequence: synthesized

<400> SEQUENCE: 15
aactggcgaa                                                              10

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence: synthesized

<400> SEQUENCE: 16
atgcgctggc                                                              10

<210> SEQ ID NO 17
<211> LENGTH: 10
<212> TYPE: DNA
<213> ORGANISM: Artificial Sequence
<220> FEATURE:
<223> OTHER INFORMATION: Description of Artificial Sequence: synthesized

<400> SEQUENCE: 17
tgccgatgaa                                                              10

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: synthesized

<400> SEQUENCE: 18
ctggaagaag                                                              10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: synthesized

<400> SEQUENCE: 19
atggcgctgg                                                              10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence: synthesized

<400> SEQUENCE: 20
atggcgatga                                                              10

<210> SEQ ID NO 21
<211> LENGTH: 17
<212> TYPE: DNA
<213> ORGANISM: Escherichia coli

<400> SEQUENCE: 21
atgctcaatc aagaact                                                      17
```

```
<210> SEQ ID NO 22
<211> LENGTH: 17
<212> TYPE: DNA
<213> ORGANISM: Escherichia coli

<400> SEQUENCE: 22
aaagttcacc acatcga                                                17

<210> SEQ ID NO 23
<211> LENGTH: 17
<212> TYPE: DNA
<213> ORGANISM: Escherichia coli

<400> SEQUENCE: 23
atgcgtaact ttgattt                                                17

<210> SEQ ID NO 24
<211> LENGTH: 17
<212> TYPE: DNA
<213> ORGANISM: Escherichia coli

<400> SEQUENCE: 24
ttagttgatt tcgatac                                                17

<210> SEQ ID NO 25
<211> LENGTH: 17
<212> TYPE: DNA
<213> ORGANISM: Escherichia coli

<400> SEQUENCE: 25
atggcagcta aagacgt                                                17

<210> SEQ ID NO 26
<211> LENGTH: 17
<212> TYPE: DNA
<213> ORGANISM: Escherichia coli

<400> SEQUENCE: 26
ctttgtccat cgcttca                                                17

<210> SEQ ID NO 27
<211> LENGTH: 17
<212> TYPE: DNA
<213> ORGANISM: Escherichia coli

<400> SEQUENCE: 27
tttaatgacc gtcgcgt                                                17

<210> SEQ ID NO 28
<211> LENGTH: 17
<212> TYPE: DNA
<213> ORGANISM: Escherichia coli

<400> SEQUENCE: 28
ccacattagc actgagt                                                17
```